United States Patent [19]

Takeguchi et al.

[11] 4,150,950
[45] Apr. 24, 1979

[54] TRANSPORT SYSTEM FOR CLINICAL SPECIMENS

[75] Inventors: Milton M. Takeguchi, Painted Post; Howard H. Weetall, Big Flats, both of N.Y.

[73] Assignee: Corning Glass Works, Corning, N.Y.

[21] Appl. No.: 837,361

[22] Filed: Sep. 28, 1977

[51] Int. Cl.$^2$ .................. G01N 33/16; A61B 10/00
[52] U.S. Cl. .................. 23/230 B; 128/2 W; 195/127; 422/102
[58] Field of Search .......... 23/259, 253 R, 230 B; 128/2 W; 195/127, 139

[56] References Cited

U.S. PATENT DOCUMENTS

| | | | |
|---|---|---|---|
| 3,163,160 | 12/1964 | Cohen | 128/2 W |
| 3,773,035 | 11/1973 | Aronoff et al. | 128/2 W |
| 3,783,106 | 1/1974 | Hensilwood | 128/2 W |
| 3,835,834 | 9/1974 | Brown et al. | 128/2 W |
| 3,890,954 | 6/1975 | Greenspan | 128/2 W |
| 3,913,564 | 10/1975 | Freshley | 128/2 W |
| 3,923,604 | 12/1975 | Monaghan | 128/2 W |
| 3,939,044 | 2/1976 | Wilkins et al. | 128/2 W |
| 3,954,563 | 5/1976 | Mennen | 195/127 |
| 3,954,564 | 5/1976 | Mennen | 195/127 |
| 4,014,748 | 3/1977 | Spinner et al. | 128/2 W |

Primary Examiner—R. E. Serwin
Attorney, Agent, or Firm—William E. Maycock; Clinton S. Janes, Jr.; Clarence R. Patty, Jr.

[57] ABSTRACT

This invention relates to means for transporting clinical specimens wherein the activity thereof can be retained for relatively long periods of time. The crux of the invention resides in a liquid reagent capable of preserving or stabilizing the activity of a particular specimen. Where the clinical specimen is *Neisseria gonorrhoeae*, the preferred liquid reagent consists of an aqueous mixture of cysteine and TRIS (Trihydroxymethylaminomethane) buffer. A convenient type of specimen collector comprises a swab. Again, where the clinical specimen is *Neisseria gonorrhoeae*, the preferred swab consists of calcium alginate. An apparatus particularly useful for transporting specimens comprises a screw-capped container having a liquid reagent sealed into the bottom portion thereof capable of preserving the activity of a particular specimen, and a specimen collector attachable to the inside of said screw cap through a longitudinal element of sufficient length to immerse said collector into said liquid. After a specimen has been obtained, the collector, attached to the screw cap, is forced through the seal into the liquid preservative as the screw cap is fastened tightly onto the container.

1 Claim, 3 Drawing Figures

TRANSPORT SYSTEM FOR CLINICAL SPECIMENS

RELATED APPLICATIONS

Patent application Ser. No. 837,366, filed of even date by H. H. Weetall entitled "Detecting Neisseria Bacteria", patent application Ser. No. 837,365, filed of even date by H. H. Weetall entitled "Comparative Test for Neisseria", patent application Ser. No. 837,364, filed of even date by H. H. Weetall entitled "Detection of Neisseria Bacteria by Immunoassay", patent application Ser. No. 837,363, filed of even date by H. H. Weetall entitled "Immunoassay of Neisseria Bacteria Via $(NH_4)_2SO_4$ Precipitation", patent application Ser. No. 837,362, filed of even date by H. H. Weetall entitled "Immunological Detection of Neisseria Bacteria Via Labelled Antibodies", and patent application Ser. No. 837,360, filed of even date by H. C. McDonald entitled "Detection and Quantitation of Neisseria Via Radioimmunoassay of an Enzyme Present in Neisseria Bacteria", each of said applications being assigned to the assignee of the instant application.

BACKGROUND OF THE INVENTION

One of the most crucial factors directly influencing the validity of a laboratory diagnostic test is the proper transport of the clinical specimen to the site where the test will be conducted. Thus, the active components of a test sample must be preserved for a sufficient length of time to permit credence to be taken of any test result. In short, a laboratory test result can only be as good as the integrity of the specimen examined.

Laboratory and field studies have indicated that, in many instances, the effective activity of components in a clinical specimen decreases precipitously, when exposed to the ambient environment, both at room temperatures and at low temperatures. For example, Table I reports experimental studies on an enzymatic test for the detection of *Neisseria gonorrhoeae* which indicated that enzymatic activity in gonococcal lysates could be essentially lost after 24 hours. Consequently, there has been a need for an efficient transport system which stabilizes and/or preserves the enzymatic activity during movement of clinical specimens.

TABLE I

| Instability of Enzymatic Activity in Lysates Stored on Cotton-Tipped Swabs | | | |
| --- | --- | --- | --- |
| | % Enzyme Activity Lost After | | |
| Storage Temp. °C. | 24 hours | 48 hours | 72 hours |
| 25 | 98 | 99 | 100 |
| −20 | 89 | 95 | 100 |

The instant invention is designed to provide such a system and is particularly described with reference to the test for *Neisseria gonorrhoeae* disclosed in the above-cited patent application Ser. No. 837,366, entitled "Detecting Neisseria Bacteria".

SUMMARY OF THE INVENTION

Figures 1, 2, 3:
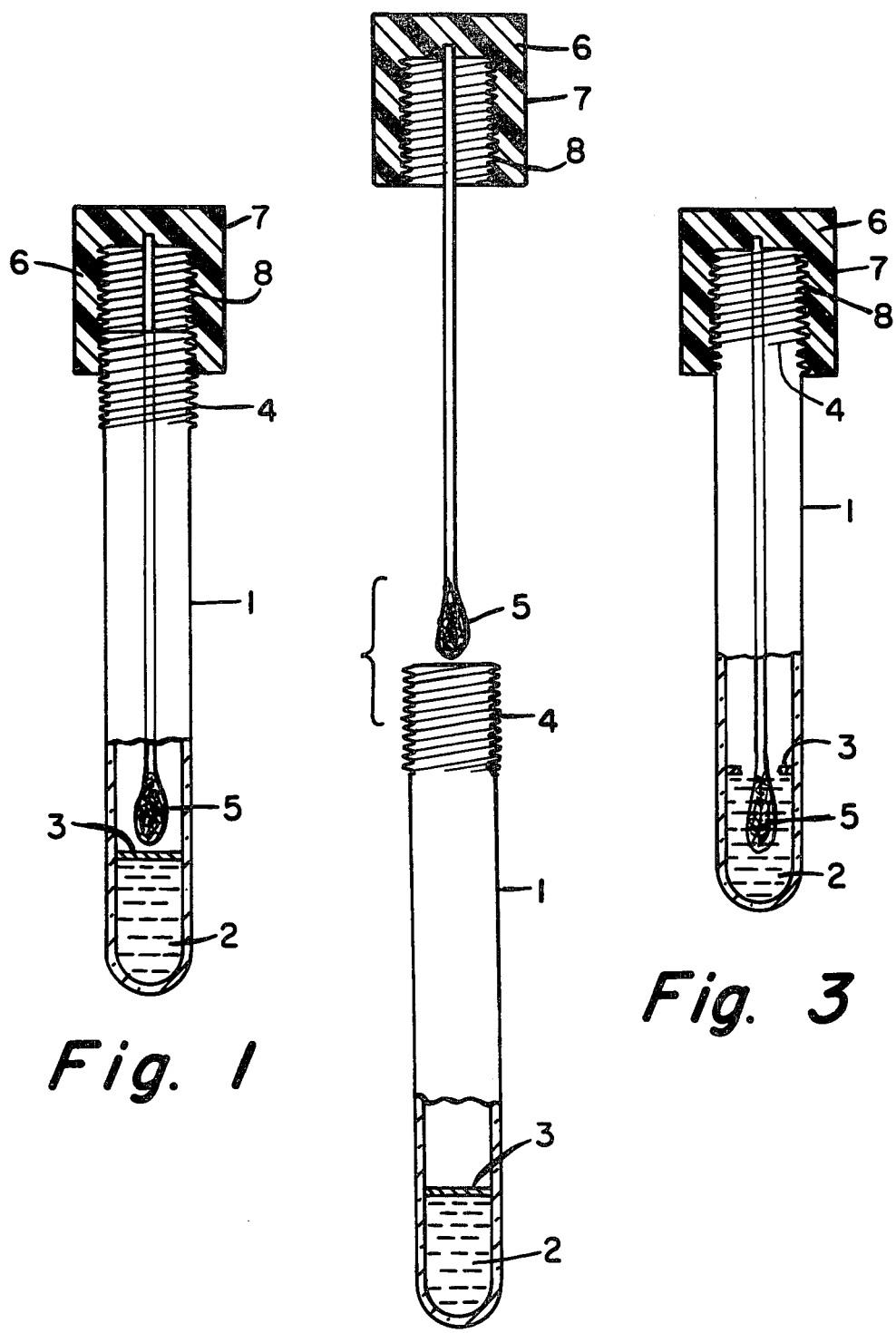
FIG. 1 is a cross-sectional view of an apparatus suitable for use in the inventive transport system preparatory to being placed in use.
FIG. 2 is a cross-sectional view of the said apparatus when a test sample is being secured.
FIG. 3 is a cross-sectional view of the said apparatus when the inventive transpost system is in use.

The inventive transport system is founded in the use of a liquid reagent having the capability of preserving or stablizing the activity of a particular specimen. As will be appreciated, certain reagents will be peculiarly suitable for various specimens. Expressed in another way, specific reagents will be preferred for specific specimens.

For example, where the clinical specimen comprises *Neisseria gonorrhoeae,* the most preferred liquid reagent consists of an aqueous mixture of cysteine and TRIS (Trihydroxymethylaminomethane) buffer. However, thiols other than cysteine, such as mercaptoethanol, dithiothreitol, and dithioerythritol, also exhibit a stabilizing influence. In general, the pH of the buffer-thiol mixture will suitably range between about 8–11.

An apparatus suitable for the inventive transport system consists of a screw-capped container having in the bottom portion thereof, a liquid reagent capable of preserving or stabilizing the activity of a particular specimen. Above the liquid reagent is a readily breakable seal which hermetically seals the liquid reagent from the remainder of the container. A specimen collector is provided which can be brought into contact with the inside of the screw cap through a longitudinal element of sufficient length to immerse the specimen collector into the liquid reagent.

In a preferred embodiment of the apparatus, the specimen collector is in the form of a swab which is suspended above the sealed liquid reagent and affixed to the inside of the screw cap. To collect a sample, the cap of the container is removed and the attached specimen collector (swab) manipulated by holding the cap. After a sample has been secured, the collector (swab) is reinserted into the container and the cap replaced thereupon. The cap is screwed through a sufficient number of threads to cause the collector (swab) to penetrate through the protective seal and become immersed in the liquid reagent. In this position the apparatus is ready for transport. Complete tightening of the cap prevents spillage of the liquid reagent and protects the container contents from the outside enviroment.

Whereas numerous swab materials are known to the art, in those instances where the clinical specimen is *Neisseria gonorrhoeae,* the preferred swab is composed of calcium alginate.

SPECIFIC EMBODIMENTS

The appended drawings are useful in understanding the operation of an apparatus operable in the present invention, but must be deemed illustrative and not limitative.

FIGS. 1–3 provide schematic representations of the preferred embodiment of the system. Thus, FIG. 1 illustrates a container 1 holding a liquid reagent 2 which is separated from the remainder of the container by seal 3. Screw-type threads 4 on the outside of container 1 extend downwardly of substantial distance from the top thereof. A sample collector (indicated as a swab) 5 is attached to the inside of screw cap 6. Screw cap 6 has a circular flange 7 of substantial length with screw-type threads on the inside thereof 8 which can be joined to screw-type threads 4. Before the system is in use, as represented in FIG. 1, the swab 5 is suspended above seal 3 since screw cap 6 is fastened to container 1 through only the first few threads of 4 and 8. The entire enclosure is sterile.

FIG. 2 is a schematic representation of the means for collecting the desired specimens. Thus, swab 5 is removed from container 1 by unscrewing cap 6. The specimen is obtained on swab 5 through manipulation of cap 6.

FIG. 3 is a schematic representation of the inventive system after a specimen has been collected and is ready for transport. Thus, after a sample has been obtained, swab 5 is replaced in container 1 and cap 6 is screwed onto container 1 via threads 8 of flange 7. Cap 6 is screwed sufficiently far down threads 4 of container 1 that swab 5 is forced through seal 3 and becomes submerged into liquid reagent 2. In such state the swab is ready for transport, the container 1 being packaged to remain in an upright position. Seal 3 may be any material which can be penetrated relatively easily, e.g., plastic, wax, or aluminum foil film, and which is inert to the liquid reagent 2 of the clinical specimen or swab 5.

As was observed above, this inventive system will be illustrated with respect to the obtaining and transport of clinical specimens to be utilized for examination for the presence of *Neisseria gonorrhoeae*.

Laboratory experiments indicated that incubation of *Neisseria gonorrhoeae* in TRIS buffer alone caused cellular lysis. This phenomenon is demonstrated in Table II where observations were made after one hour at 4° C.

TABLE II

| Suspending Medium | Phase Microscopy Observations | |
|---|---|---|
| | % Intact Cells | % Lysed Cells |
| Physiological saline | 99.0 | 1.0 |
| TRIS Buffer | 1.0 | 99.0 |
| TRIS + EDTA | 1.0 | 99.0 |
| TRIS + Lysozyme | 1.0 | 99.0 |
| TRIS + EDTA + Lysozyme | 1.0 | 99.0 |

As was manifested above in Table I, however, the enzymatic activity in these lysates decreased significantly after relatively short periods of storage.

Various chemical compounds were incorporated into the TRIS buffer and numerous gonococcal lysates were prepared. These lysates were stored and tested to study the effect, if any, such compounds had in stabilizing the enzyme. Table III records the results of those tests.

TABLE III

| Lysis of Neisseria gonorrhoeae | |
|---|---|
| Compound | % Enzyme Activity Recovered After 24 Hour Storage at −20° C. |
| Control | 11 |
| Ascorbic Acid | ≦60 |
| Cysteine | 89 |
| Mannitol | ≦60 |
| 5-5 dithiobis-(2 nitrobenzoic acid) | 0 |
| 4-chloromercuric benzoic acid | 67 |
| Glutaraldehyde | 0 |
| Cellulose Gum | ≦20 |
| Polyethylene Glycol | 0 |
| AMP (adenosine monophosphate) | 6 |

It is quite apparent that cysteine exhibited the most stabilizing influence upon enzymatic activity in lysates derived from *Neisseria gonorrhoeae*. Accordingly, similar thiol compounds, for example, mercaptoethanol, dithiothreitol, and dithioerythritol, can also be effective for this purpose. In general, these thiol compounds are used in concentrations between about 0.01–0.1M.

Table IV reports the preferred liquid reagent solution for the stabilization of enzymatic activity in gonococcal lysates.

TABLE IV

| Ingredient | Amount |
|---|---|
| TRIS base | 12.1 g |
| L-cysteine hydrochloride | 0.175 g |
| H$_2$O | 1000 ml |

A comparison was made between the recovery of enzymatic activity in specimens stored on cotton swabs with that exhibited by specimens stored on calcium alginate swabs. Table V clearly demonstrates that the samples stored on calcium alginate swabs retained greater activity for longer periods of time than samples stored on cotton swabs.

TABLE V

| Swab | % Recovery of Enzyme Activity After Time | | |
|---|---|---|---|
| | 20 Hours | 45 Hours | 116 Hours |
| Cotton | 25 | 0 | 0 |
| Calcium Alginate | 40 | 40 | 27 |

In summary, the preferred embodiment of the instant invention provides a clinical specimen transport system which (a) contains a reagent which lyses *Neisseria gonorrhoeae*, (b) contains a swab and reagent which promote stabilization or preservation of enzymatic activity in the lysate, and (c) allows recovery of the enzymatic activity after a storage period of several days.

Although this inventive transport system has been illustrated with specific utility with respect to the collection and transport of clinical specimens for the detection of *Neisseria gonorrhoeae*, it will be recognized that the system can be employed with other specimens. Furthermore, whereas the system has been discussed with particular regard to FIGS. 1-3, it will be recognized that various modifications in design are envisioned which adhere to the spirit of the invention. For example, in FIGS. 1-3 specimen collector 5 is pictured as being integrally attached to cap 6. Such is not necessary, of course, but it has the advantage of convenience. Likewise, the use of a swab as a specimen collector is a matter of practical convenience but is not required. Also, FIG. 3 shows cap 6 fully screwed onto container 1. However, the movement of collector 5 need only be so far as to become immersed into liquid reagent 2.

Hence, the sole requirements of the inventive transport system are three: viz.; (1) a container for holding a liquid reagent sealed into the bottom portion thereof, the liquid reagent being capable of preserving or stabilizing the activity of a particular specimen and allowing recovery of specimen activity after a period of storage; (2) a specimen collector; and (3) means for causing the specimen collector to become immersed into the liquid reagent. In general, specimen activity refers to enzymatic activity.

We claim:

1. A method for the transport of a clinical specimen of *Neisseria gonorrhoeae* wherein said speciment is immersed in a liquid reagent capable of stabilizing or preserving the activity of said specimen, which liquid reagent has a pH of from about 8 to about 11 and is composed of TRIS buffer and a thiol selected from the group consisting of cysteine, mercaptoethanol, dithiothreitol, and dithioerythritol.

* * * * *